(12) United States Patent
Znamenskiy et al.

(10) Patent No.: US 9,586,017 B2
(45) Date of Patent: Mar. 7, 2017

(54) CUSTOMIZABLE USER INTERFACE DEVICE FOR USE WITH RESPIRATORY VENTILATION SYSTEMS

(71) Applicant: KONINKLIJKE PHILIPS N.V., Eindhoven (NL)

(72) Inventors: Dmitry Nikolayevich Znamenskiy, Eindhoven (NL); Ruud Vlutters, Eindhoven (NL); Karl Catharina Van Bree, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 328 days.

(21) Appl. No.: 14/356,642

(22) PCT Filed: Nov. 7, 2012

(86) PCT No.: PCT/IB2012/056241
§ 371 (c)(1),
(2) Date: May 7, 2014

(87) PCT Pub. No.: WO2013/068950
PCT Pub. Date: May 16, 2013

(65) Prior Publication Data
US 2014/0326243 A1  Nov. 6, 2014

Related U.S. Application Data

(60) Provisional application No. 61/557,566, filed on Nov. 9, 2011.

(51) Int. Cl.
*A61M 16/06* (2006.01)
*A61M 16/00* (2006.01)

(52) U.S. Cl.
CPC .... *A61M 16/0622* (2014.02); *A61M 16/0057* (2013.01); *A61M 16/06* (2013.01);
(Continued)

(58) Field of Classification Search
CPC .............. A61M 16/0057; A61M 16/06; A61M 16/0605; A61M 16/0611; A61M 16/0616;
(Continued)

(56) References Cited

U.S. PATENT DOCUMENTS 6,712,072 B1  3/2004 Lang
6,728,589 B1  4/2004 Delache et al.
(Continued)

FOREIGN PATENT DOCUMENTS

CN  1735438 A  2/2006
CN  101249293 A  8/2008
(Continued)

OTHER PUBLICATIONS

"Soft Elastomeric Materials for Fused Deposition Modeling (FDM); Custom Fit Oxygen Face Masks", http://cadserv.cadlab.vt.edu/bohn/rp/elastomer/masks.html, Aug. 4, 1997, 2 pages.
Shapeways Blog—Introducing White Strong & Flexible, May 9, 2011.

*Primary Examiner* — Annette Dixon
(74) *Attorney, Agent, or Firm* — Michael W. Haas

(57) ABSTRACT

The present invention provides a cost effective customization of user interface devices for use with respiratory ventilation systems, such as face masks that may be used for CPAP therapy. By integrating a user specific customize element (15) into a pre-fabricated user interface device (10), increased comfort for a user during use of the interface device (10) is provided. The customized element (15) is adapted to affect the shape of the user interface device making it compliant with at least one user specific body feature, for example, a facial feature of a particular user. The shape of the customized element may be computed from a user specific data set representing an e.g. three-dimensional shape at least one body feature of a user.

12 Claims, 9 Drawing Sheets

(52) U.S. Cl.
CPC . *A61M 16/0611* (2014.02); *A61M 2016/0661* (2013.01); *Y10T 29/49826* (2015.01)

(58) Field of Classification Search
CPC .......... A61M 16/0622; A61M 16/0633; A61M 16/0638; A61M 16/0683; A61M 16/08; A61M 16/0825; A61M 2207/00; A62B 18/08; B29C 45/0001; B29C 65/00; B29C 65/02; B29C 65/028; B29C 65/04; B29C 65/48; B29C 66/21; B29C 66/324; B29C 67/246; B29C 69/004; B29K 2075/00; B29K 2083/00; B29K 2105/0061; B29K 2283/00; B29L 2022/025; B29L 2031/4835; Y10T 29/49; Y10T 29/4987
USPC ............ 128/205.25, 206.21, 206.24, 206.26, 128/206.28, 207.14, 207.17
See application file for complete search history.

(56) References Cited

U.S. PATENT DOCUMENTS

| | | | |
|---|---|---|---|
| 7,958,893 B2 | 6/2011 | Lithgow et al. | |
| 2004/0118406 A1* | 6/2004 | Lithgow | A61M 16/06 128/206.24 |
| 2005/0199239 A1* | 9/2005 | Lang | A61M 16/06 128/206.24 |
| 2007/0215161 A1* | 9/2007 | Frater | A61M 16/06 128/206.24 |
| 2008/0078396 A1 | 4/2008 | Janbakhsh | |

FOREIGN PATENT DOCUMENTS

| | | |
|---|---|---|
| WO | WO9709090 | 3/1997 |
| WO | WO2011003128 | 1/2011 |

* cited by examiner

CUSTOMIZABLE USER INTERFACE DEVICE FOR USE WITH RESPIRATORY VENTILATION SYSTEMS

CROSS-REFERENCE TO PRIOR APPLICATIONS

This application is the U.S. National Phase application under 35 U.S.C. §371 of International Application Serial No. PCT/IB2012/056241, filed on Nov. 7, 2012, which claims the benefit of U.S. Application Ser. No. 61/557,566, filed on Nov. 9, 2011. These applications are hereby incorporated by reference herein.

FIELD OF THE INVENTION

The present invention relates to user interface devices for delivering a gas to an airway of a user, and associated methods and systems.

BACKGROUND OF THE INVENTION

Non-invasive respiratory ventilation and pressure support therapies involve the placement of a user interface device, which is typically a nasal or nasal/oral mask, on the face of a user, such as a patient, to interface the respiratory ventilation or pressure support system with the airway of the patient so that a flow of breathing gas can be delivered from the pressure/flow generating device to the airway of the patient.

In recent years, continuous positive air pressure (CPAP) therapy, a method of respiratory ventilation, has become a common treatment for individuals suffering from sleep disorders such as obstructive sleep apnea (OSA) or other breathing ailments. The positive pressure air may be delivered to the patient's upper airway to prevent the upper airway tissues from collapsing during sleep, thus reducing the occurrence and/or severity of sleep apnea. A user interface device, such as nasal or nasal/oral mask, is typically used to deliver continuous positive air pressure (CPAP) to the user.

Such a user interface device must have an effective seal, needs to be held on securely, and may be worn by the user, such as a patient, over extended periods of time, for example, during the night while sleeping or during the day when working in an emergency situation. Therefore, the user interface device should be as comfortable as possible. Otherwise the patient may avoid wearing the interface device. This can defeat the purpose of the pressure support therapy or expose the wearer to dangers from toxins for example. It is also important that the user interface device provides a tight enough seal against a patient's face without discomfort. A problem arises in that in order for the mask to maintain a seal without any undue gas leaks around the periphery of the mask, the mask cushion may be compressed against the patient's face. This is most notable, for example, in masks having a bubble type cushion. While the bubble cushion itself is comfortable, it does not provide adequate support, which may cause gas leaks around the periphery of the mask. The bubble effect is diminished when the headgear strap force is increased to improve stability.

An additional disadvantage of conventional user interface devices is, for example, that conventional masks may form a poor seal with the face of a patient, because many mask assemblies conform to only standard sizes and shapes. For example, conventional masks may not account for differences in the sizes or shapes of the facial features of different patients, thus causing discomfort or pain. Still further, because of the poor seals or fits often associated with conventional masks, the mask may not stay in place, and may shift or move, while in use and may fail to adequately prevent leakage. Accordingly, such user interface devices or masks should be made soft enough to adapt to different face geometries, should stay on compliant under pulling of the hose aside, should be rigid enough to hold the mask on the same place on the face during use, and should not leak under the working air pressure.

In severe cases, patients wearing a typical face mask as well known in the art may develop skin irritation or even wounds from wearing the mask. One reason for this is that pressure points may develop while wearing the mask. As there are many differences between human faces, it is very difficult to develop a limited number of masks that should fit everyone. For optimal comfort, a mask should ideally be customized to fit its user's face, but currently, involved costs prohibit this.

A prior art approach to conform the periphery of a mask cushion to the contours of a user's face is to include a pliable wire into or adjacent to the cushion, as disclosed, for example, in U.S. Pat. No. 7,958,893 B2. It is relatively difficult to adjust a wire to the contours of a face by bending the wire. Furthermore, the wire may not capable of holding a certain form over long periods of time, especially with mechanical impact to the wire, for example, during the movements of a user while sleeping. Unintended bending of the wire may then lead again to undesired pressure points. Still further, prolonged bending of such a wire may lead to damage or breakage of the wire, which would make a mask cushion containing the wire unusable.

SUMMARY OF THE INVENTION

It is an object of the present invention to provide a customizable user interface device for delivering a gas to an airway of a user, such as, but not limited to, masks for respiratory ventilation systems to be worn by a user or patient on the face. An advantage of embodiments of the present invention is an improvement in personalization of a user interface device for use with respiratory ventilation systems, such as personalization of face masks that may be used for CPAP therapy, BiPAP (Bi-level Positive Airway Pressure) or similar therapy regimes, in particular, improvement of the personalization of a facial interface. It is a further advantage of embodiments of the present invention to provide a cost effective customization of user interface devices.

Another advantage of embodiments of the present invention is that enabling customization of an otherwise standard user interface device results in an improved fit of the user interface device during use and, thus, increased comfort for a specific user. A further advantage of embodiments of the present invention is that the customized element may be the only custom fabricated element of an otherwise standard device.

The above objective is accomplished by a device, a method, and a system according to the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

According to the advantageous embodiments of the present invention, a customizable user interface device for delivering a gas to a user comprises a surface interface adapted for fitting to at least on body feature specific to the user. The user interface device is adapted for receiving a customized element for affecting the shape of the surface interface according to the at least one body feature specific to the user. It is advantageous that the user interface device is customizable, since that way the user interface device is provided separately from the customized element. Thus, it is possible to combine a customized element specific to a user with a variety of user interface devices, which results in improved comfort for the user.

In accordance with a further embodiment of the present invention, a user interface device for delivering a gas to a user and having an surface interface adapted for fitting to at least one user specific body feature, comprises a customized element adapted for customizing the user interface device, and means for connecting the customized element with at least one part of the user interface device. The customized element is adapted to affect the shape of the surface interface according to the at least one user specific body feature. Thus, there is a correspondence between the shape of the customized element and the at least one user specific body feature. It is advantageous that due to its shape the customized element provides a customized pressure distribution at the surface interface and, thus, a customized and improved fit of the user interface device during use resulting in increased comfort for the user. The at least one user specific body feature comprises a feature of the user's face. The means for connecting the customized element with the at least one part of the user interface device may include, for example, provisions for embedding the customized element within the user interface device, such as a chamber positioned within the at least one part of the user interface device, or provisions for surface mounting the customized element, such as mechanical connectors or adhesives. The at least one part of the of the user interface device may be a cushion, a forehead support, an outline of the entire user interface device, or a nasal-mouth area.

In accordance with a further embodiment of the present invention, the user interface device for delivering a gas to a user and having an surface interface adapted for fitting to at least one user specific body feature, comprises a customized element adapted for customizing the user interface device, and a connector adapted for joining the customized element with at least one part of the user interface device.

In further embodiments of the present invention, the shape of the customized element is adapted based on a user specific data set representing an shape, e.g. a three-dimensional shape of the at least one user specific body feature. The user specific data set may be obtained, for example, from a three-dimensional scan. The three-dimensional scan may be, for example, an optical scan. The user specific data set may be supplemented with measurement data of the thickness and sensitivity of the skin of the user in the area of the three-dimensional scan. It is an advantage that a relatively high degree of customization is reached.

In still further embodiments of the present invention, the customized element consists of several parts. The customized element may further be formed as a single part. The customized element is fabricated from a metallic spring material or preferably plastic. The customized element may be fabricated using various rapid prototyping technologies (e.g. Selective Laser Sintering) or by modifying the shape of a mass-produced blank element. This is advantageous since the most cost effective combination of material and manufacturing method can be selected. The shape of the customized element is either changeable or not changeable after being first adapted to have a shape according to at least one user specific body feature. This is advantageous since it increases the customizability of the user interface device.

In still further embodiments of the present invention, the at least one part of the user interface device includes a chamber for receiving the customized element. The chamber may be positioned between a support interface and a surface or facial interface. The chamber can be placed at variable distance from the skin. The distance to the skin surface can be larger in the areas with extra thin and sensitive skin. The chamber may further include an opening adapted for insertion and removal of the customized element, wherein the opening is preferably positioned on an outer surface of the at least one part of the user interface device and, therefore, outside of the breathing path, to prevent the customized element from contact with the breathing volume inside the user interface device. This is advantageous since the customized element is not exposed the bacteria or moisture that may be in the breathing path.

In still further embodiments of the present invention, a customized element adapted for connection with a user interface device for delivering a gas to a user comprises a pre-formed structure, e.g. a three-dimensional structure, adapted to affect the shape of the user interface device according to at least one body feature specific to the user. Thus, the customized element has a shape that corresponds with the at least one body feature specific to the user. The embodiments bring the advantage that the customized element may provide a pressure distribution on the side of the surface interface (optimized for maximum comfort) that is different from the pressure distribution of the side of a support interface (optimized for better flexibility of the support). For example, in gas mask applications, the customized element can receive an extra pressure from the support interface in highly sensitive nose-bridge and chin areas and re-distribute this pressure in less sensitive areas on the forehead and sides of the face. The customized element can be placed at variable distance from the skin. The distance to the skin surface can be larger in the areas with extra thin and sensitive skin. Furthermore, the customized element can be pre-shaped in accordance to an average shape of a specific body feature where the average is taken over a certain population of people (e.g. OSA patients, Asian faces, Afro-American faces, etc.). It is an advantage that with the customized element an improved fit of the user interface device during use is enabled.

In still further embodiments of the present invention, a method of customizing a user interface device for delivering a gas to a user or of manufacturing a customized element for affecting the shape of a surface interface comprised in a user interface device for delivering a gas to a user, the user interface device having a surface interface adapted for fitting to at least one user specific body feature, comprises the steps of providing a user specific data set representing an e.g. three-dimensional shape of the at least one user specific body feature and manufacturing a customized element according to the user specific data set such that the customized element is adapted to affect the shape of the surface interface. Further steps may include connecting the customized element with the user interface device and deforming the user interface device according to the user specific data set. A still further step may include manufacturing the customized element utilizing a rapid prototyping technology or modifying the shape of a mass-produced blank element. The data set may be provided from a data storage device such as a CD-ROM, a DVD-ROM, a solid state memory such as a USB memory stick or via a network such as a Local Area Network (e.g. a LAN in a hospital) or a wide area data network like the Internet. It is an advantage that with such a method cost effective customization of an otherwise standard user interface devices is enabled. It is a further advantage that by providing user specific data a high degree of customization can be reached resulting in increased comfort for users.

In embodiments of the present invention, the method of customizing a user interface device may still further include the step of utilizing the customized element to keep the user interface device compliant with the at least one body feature of the user under a wide range of deformations of the user interface device. This is an advantage in such that extra freedom may be provided to the position of the user interface device relative to a user's face and the range of applied air pressures. Still further included in the method may be the steps of removing the customized element from the at least one part of the user interface device and reusing the customized element in a second user interface device. This is advantageous since the customized element can be used in a variety of user interface masks worn by the same user.

In still further embodiments of the present invention, a system for manufacturing a user interface device or for manufacturing a customized element for affecting the shape of a surface interface comprised in a user interface device for delivering a gas to a user or for customizing the user interface device comprises equipment adapted to receive user specific data representing an e.g. three-dimensional shape of at least one user specific body feature and manufacturing equipment adapted to produce a customized element in accordance to the user specific data. The shape of the customized element does not have to follow the data or the contour of the user specific body feature exactly, but there is a correspondence between the data and the shape of the customized element such that, when used in a user interface device, the customized element affects the shape in an interface surface to better fit a user specific body feature. Fitting does not necessarily mean that the interface surface follows the contour of the user specific body feature. The system may, for example, receive the user specific data by receiving an already existing data set representing the shape of the user specific body feature. The system may be able to obtain a data set by itself instead of, or in addition to receiving an already existing dataset. To this end, the system may further include equipment adapted to obtain user specific data representing an e.g. three-dimensional shape of at least one user specific body feature and/or equipment adapted to obtain measurement data of the thickness and sensitivity of the skin of the user in the area of the at least one body feature to obtain additional user specific data to be utilized by the manufacturing equipment. The system may, for example, obtain the user specific data by performing a measurement on the user resulting in a data set representing a shape of the user specific body feature. The system may comprise equipment for manufacturing a user interface device for receiving a customized element according to the present invention and/or equipment for combining together a user interface device and a customized element according to the invention.

In still further embodiments of the present invention, a customizable cushion assembly for a user interface device is provided that includes a cushion having a facial interface portion adapted for contacting a user's face, and a holder element coupled to the cushion, the holder element being structured to removeably receive and hold a customized element in a manner wherein the customized element when held by the holder element affects a shape of the facial interface portion according to at least one body feature specific to the user. In one exemplary embodiment, the holder element is made of a material that is harder than the material of the cushion, and the holder element is integrally formed as part of the cushion during molding of the cushion.

In still another embodiment of the present invention, a method of customizing a user interface device is provided that includes steps of providing a customized element comprising a preformed structure having a first shape determined based on at least one user specific body feature, and of coupling the customized element to a customizable cushion assembly, wherein the customizable cushion assembly includes: (i) a cushion having a facial interface portion adapted for contacting a user's face, and (ii) a holder element coupled to the cushion, wherein the customized element is removeably received and held by the holder element in a manner wherein the customized element affects a second shape of the facial interface portion according to the first shape of the customized element.

In still further embodiments of the present invention, acustomized element for a user interface device including a customizable cushion assembly is provided, wherein the customizable cushion assembly includes: (i) a cushion having a facial interface portion adapted for contacting a user's face, and (ii) a holder element coupled to the cushion, the customized element comprising a preformed structure having a first shape determined based on at least one user specific body feature, the customized element being structured to be removeably received and held by the holder element in a manner wherein the customized element affects a second shape of the facial interface portion according to the first shape of the customized element. In one embodiment, the customized element includes an internal groove structured to receive and hold an enlarged portion of the holder element, and in another, alternative embodiment, the holder element comprises a portion defining a channel, and the customized element has a cross-sectional shape that is complimentary to a shape of the channel to enable the portion to receive and hold the customized element.

The above and other characteristics, features, and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
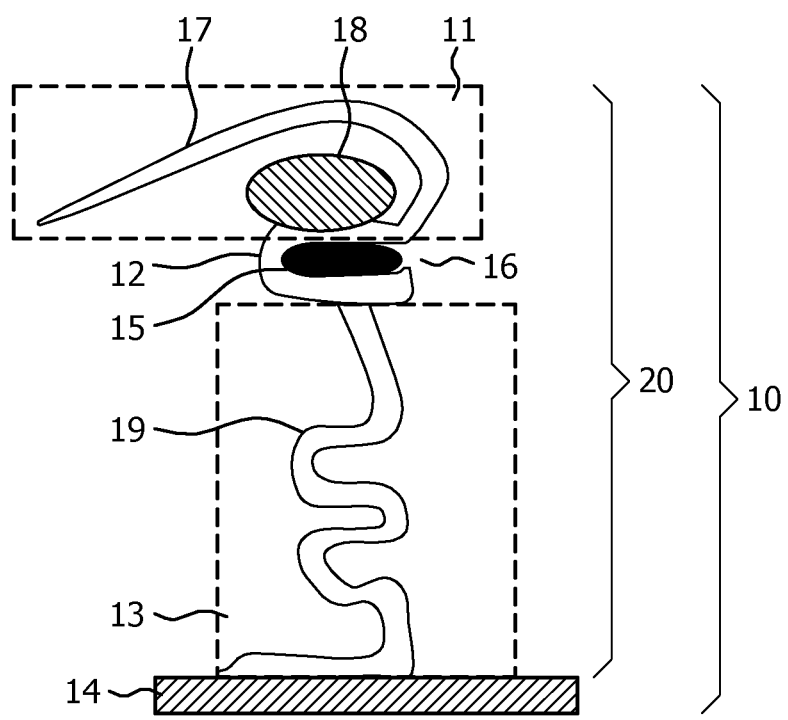
FIG. 1 is a schematic cross-section of a user interface device, in accordance with an embodiment of the present invention.

In the different figures, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms or definitions are provided solely to aid in the understanding of the invention.

As employed herein, the term "interface" refers to a surface forming a common boundary between adjacent regions or bodies.

Furthermore, the term "user interface device for delivering gas to a user" refers to any suitable mechanism for transporting gas to and/or from the airway of a user, such as a patient, the gas may be pressurized (e.g., positive airway pressure) or may not be pressurized, and expressly includes, but is not limited to, non-invasive respiratory interfaces such as masks (e.g., without limitation, masks including support elements such as forehead supports and cheek pads and full face masks).

Still further, the term "cushion" refers to a flexible structure provided to a substantially rigid or semi-rigid frame member and adapted to engage with the user's face. A "cushion" may engage with certain areas of a user's face such as the chin area, the mouth area, the nasal area, the nasal-mouth area, the forehead area or may outline of the entire user interface device.

In embodiments of the present invention, the customized element may be easily joint with and removed from the user interface device allowing re-usage of one customized element with other user interface devices or, for example, with multiple disposable cushions of such devices. On the other hand, a single user interface device may be used with a variety of customized elements to be used by different users. The customized element is adapted to affect the shape of a facial interface and to provide a customized pressure distribution at the facial interface.

Referring to FIG. 1, a user interface device 10 for delivering a gas to an airway of a user is illustrated in accordance with embodiment s of the present invention. The user interface device 10 includes a cushion 20 adapted for contacting the user's face, a base 14, a customized element 15, and means for joining the customized element 15 with the cushion 20. The customized element 15 affects at least partially the shape of the cushion 20. Cushion 20 is a flexible structure provided to a substantially rigid or semi-rigid frame member, the base 14, and adapted to engage with the user's face. The cushion 20 may engage with certain areas of a user's face such as the chin area, the mouth area, the nasal area, the nasal-mouth area, the forehead area or may outline of the entire user interface device.

Cushion 20 includes a facial interface 11 adapted for contacting the user's face and a support interface 13 positioned between the facial interface 11 and the base 14. The facial interface 11 is typically optimized for maximum comfort for the users and support interface 13 is typically optimized for flexibility of the cushion 20. The facial interface 11 includes a core 18 adapted for providing flexibility and strength and is made of a deformable material, such as, for example, a polymer. The facial interface 11 further includes an integrated air tight-flap 17 adapted to engage with the user's face. In alternative embodiments, the air-tight flap 17 can be a separate part. Do to the usage of customized element 15, the facial interface 11 does not have any controlling function for the shape of cushion 20 and, therefore, can be made from a flexible material to be extra soft. The support interface 13 includes a core 19 adapted for providing flexibility and strength. The core 19 is made of a deformable material, such as, for example, a polymer and can contain spring like elements embedded in such material. Support interface 13 is mechanically connected with the base 14 of the user interface device 10.

Cushion 20 further includes a chamber 12 adapted for receiving the customized element 15. Chamber 12 may be positioned between support interface 13 and facial interface 11 along the periphery of cushion 20. Chamber 12 may include an opening 16 adapted to allow insertion and removal of customized element 15. Opening 16 of chamber 12 is preferably positioned outside of the breathing path on the outer surface of cushion 20, as shown in FIG. 1, to secure customized element 15 inside chamber 12 when the user interface device expands under the air pressure provided by a respiratory ventilation system. Furthermore, by positioning opening 16 of chamber 12 on the outer surface of cushion 20 and, therefore, outside of the breathing path, customized element 15 may be prevented from contact with the breathing volume inside the user interface device allowing a more flexible design of element 15.

Customized element 15 comprises a pre-formed rigid or semi-rigid structure adapted for corresponding to the shape of the user's face and adapted for extending at least partially along a contour of the user interface device 10. The rigid structure has no direct contact with the user's face and the gas. The shape of the structure is based on a user specific data set representing an e.g. three-dimensional shape of the user's face. In one embodiment, the shape of the structure is not changeable after being first pre-formed according to the shape of the user's face.

Customized element 15 is fabricated independently and separately from the user interface device 10 and may be positioned within chamber 12 at a certain distance from the integrated air-tight flap 17 (as shown in FIG. 1) The customized element 15 can be placed at variable distance from the user's face. The distance to the user's face and, thus, the skin surface can be larger in facial areas with extra thin and sensitive skin.

Customized element 15 is adapted to be relatively rigid or semi-rigid and is responsible for the optimal pressure distribution at the facial interface 11 of the user interface device 10. Customized element 15 is adapted to pre-deform cushion 20, and specifically the facial interface 11, making it compliant with a given face of a particular user. Customized element 15 is a custom fabricated element, where the shape is adapted to match a user specific data set representing an e.g. three-dimensional shape of the user's face. The data set may be, for example, obtained from a three-dimensional (3D) scan of the user's face, such as a facial scan. The data set can include data from the entire face of the user or only from certain parts, such as the nose, chin, forehead, or cheeks. The scan may be an optical, MRI, CT, X-ray, PET, sonar scan or similar from which a 3D-surface image of the at least one user specific body feature can be obtained. The e.g. three-dimensional shape of the at least one user specific body feature may also be obtained, for example, by first making a cast of the body part and then making a scan of the inside of the cast. An advantage of this latter method is that higher energy scanning beams can be used than are allowed for application to human beings. Other methods to obtain the data set may include, for example, pins adapted to follow the contour of the shape of the at least one user specific body feature. The collected data can be stored on a data storage device such as a CD-ROM, a DVD-ROM, a solid state memory such as a USB memory stick or can be provided via a network such as a Local Area Network (e.g. a LAN in a hospital) or a wide area data network like the Internet. The optimal shape of customized element 15 can be computed from the projection of the facial interface 11 on the 3D facial scan of the user, taking into account the thickness and rigidity of the pre-fabricated cushion 20.

Customized element 15 may be fabricated from a metallic spring material or preferably plastic using, for example, a custom pressing. Alternatively, customized element 15 may be made using a rapid prototyping technique such as NC milling or any plastic or metal layered manufacturing technique such as 3D printing, stereo lithography (SLA), Selective Laser Sintering (SLS), Fused Deposition Modelling (FDM), foil-based techniques, etc. Since customized element 15 does not have contact with the skin of a user, it may be produced from a broad range of materials. Customized element 15 may be made from a 3D printable material, for example, from a relatively strong nylon material having a relatively good heat resistance, such as Nylon 12 or Polyamide PA 2200 using selective-laser-sintering (SLS). Nylon 12 and Polyamide PA 2200, for example, are common materials used in SLS and parts made of these materials have good long term stability, offering resistance to most chemicals. These materials are harmless to the environment and safe to use with food articles. Complexity is irrelevant and the materials deliver the impact strength and durability required for functionality. Tensile and flexural strength combine to make tough plastic prototypes, with the flex associated with many production thermoplastics. It is able to emulate living hinge designs, certainly to 20+ cycles. These plastic materials are non-hygroscopic, thereby negating the requirement to seal the surface on components being used with liquids.

In on embodiment, cushion 20 is pre-fabricated standard article. For example, cushion 20 can be a typical standard cushion adapted for use with known user interface devices. Cushion 20 can be part of a user interface device, such as a face mask, used with a respiratory ventilation system, for example, for continuous positive air pressure (CPAP) therapy. Since typical standard cushions exist in different size categories, such as small, medium, large, etc., customized element 15 may be fabricated according to these size categories.

Figure 2:
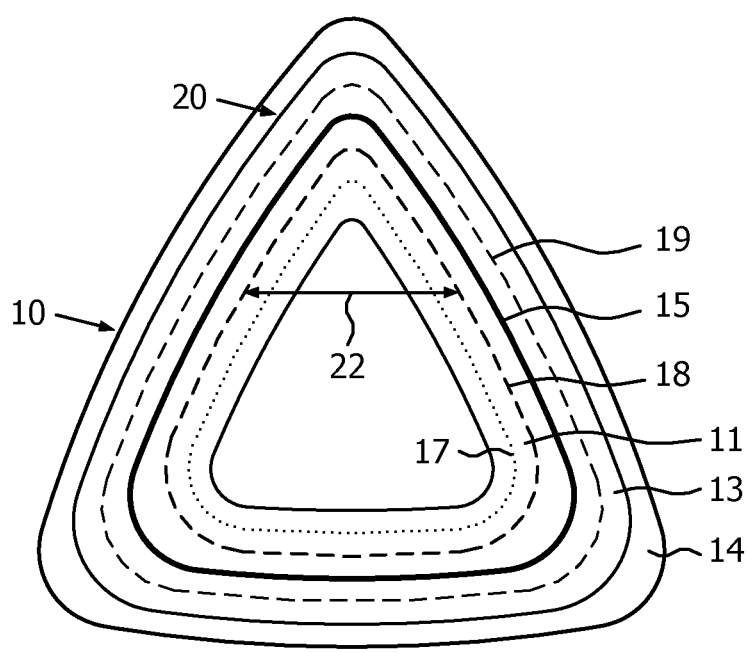
FIG. 2 is a schematic top view of the user interface device as shown in FIG. 1.

Referring to FIG. 2, a schematic top view of the user interface device 10 is illustrated in accordance with embodiments of the present invention. The user interface device 10 includes a cushion 20 adapted for contacting the user's face, a base 14, a customized element 15, and means for joining the customized element 15 with the cushion 20. Cushion 20 is a flexible structure provided to a substantially rigid frame member, the base 14, and adapted to engage with the user's face. Cushion 20 includes a facial interface 11 adapted for contacting the user's face and a support interface 13 positioned between the facial interface 11 and the base 14. The facial interface 11 includes a core 18 adapted for providing flexibility and strength. The facial interface 11 further includes an integrated air tight-flap 17 adapted to engage with the user's face. The support interface 13 includes a core 19 adapted for providing flexibility and strength.

As can be see, the customized element 15 extends along the contour of the interface device 10, and specifically, of the cushion 20. According to the first example, the customized element 15 is formed as a single part adapted to have the shape of a ring. The cross-section of the ring can be elongated in the direction tangent to the user's face to control the local shape of the facial interface 11 and provide better comfort. Customized element 15 is shown in FIG. 2 to be adapted as a single part.

Furthermore, horizontal forces 22 are illustrated to indicate horizontal deformation of the cushion 20. Here horizontal means in the facial plane. The horizontal forces 22 can have an impact on the facial interface 11 and/or the support interface 13.

Figure 3:
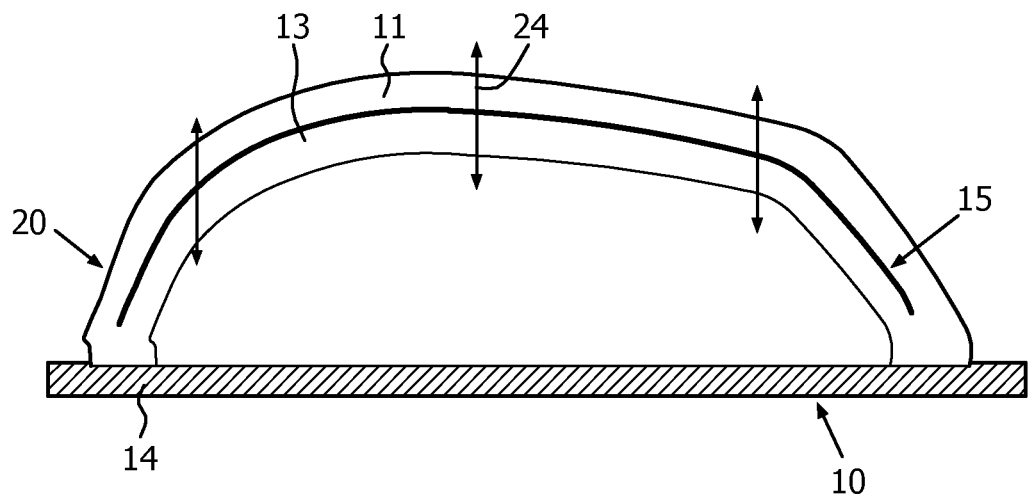
FIG. 3 is a schematic side view of the user interface device as shown in FIG. 1.

Referring to FIG. 3, a schematic side view of the user interface device 10 is illustrated in accordance with embodiments of the present invention. The user interface device 10 includes a cushion 20 adapted for contacting the user's face, a base 14, a customized element 15, and means for joining the customized element 15 with the cushion 20. Cushion 20 is a flexible structure provided to a substantially rigid frame member, the base 14, and adapted to engage with the user's face. Cushion 20 includes a facial interface 11 adapted for contacting the user's face and a support interface 13 positioned between the facial interface 11 and the base 14. Furthermore, vertical forces 24 are illustrated to indicate vertical deformation of the cushion 20. Here vertical means orthogonal to the facial plane. The vertical forces 24 can have an impact on the facial interface 11 and/or the support interface 13.

Figure 4:
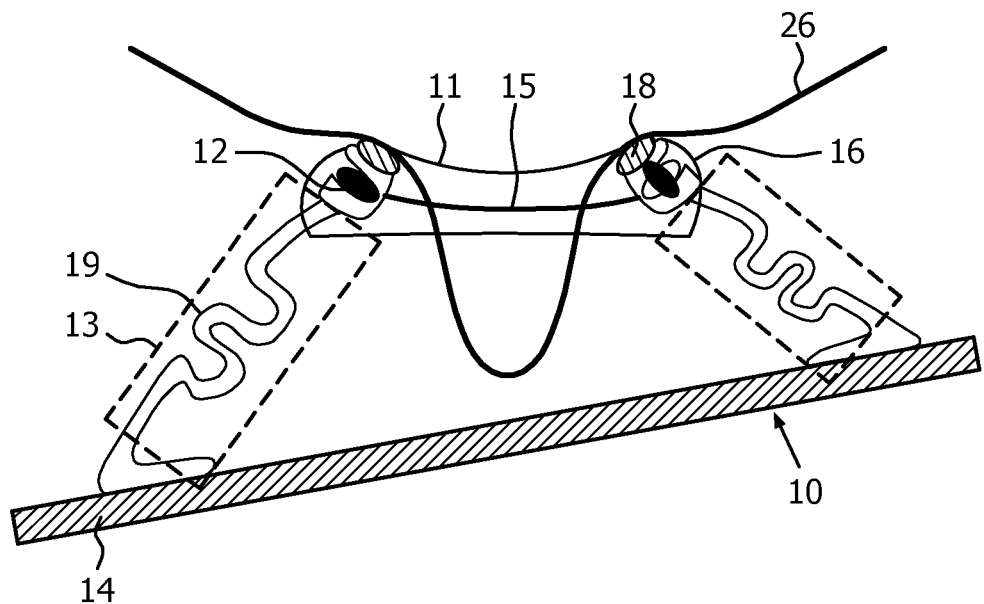
FIG. 4 is a schematic side view of the user interface device as shown in FIG. 1 under deformation due to pulling the user interface device aside.

Referring to FIG. 4, a schematic side view of the user interface device 10 under deformation due to pulling the user interface device aside is illustrated in accordance with embodiments of the present invention. The user interface device 10 includes a cushion 20 adapted for contacting the user's face, a base 14, a customized element 15, and means for joining the customized element 15 with the cushion 20. Cushion 20 is a flexible structure provided to a substantially rigid frame member, the base 14, and adapted to engage with the user's face. Cushion 20 includes a facial interface 11 adapted for contacting the user's face and a support interface 13 positioned between the facial interface 11 and the base 14. The facial interface 11 includes a core 18 adapted for providing flexibility and strength. The facial interface 11 further includes an integrated air tight-flap 17 adapted to engage with the user's face. The support interface 13 includes a core 19 adapted for providing flexibility and strength. A pressure distribution line 26 representing the pressure distribution at the facial interface 11 is shown for deformation of the user interface device 10 when pulled aside.

Figure 5:
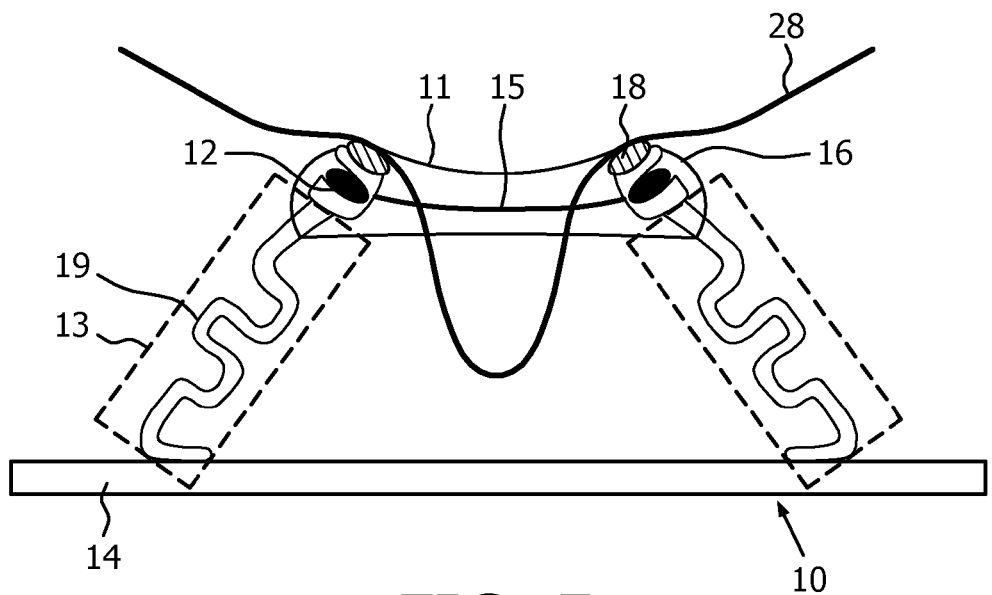
FIG. 5 is a schematic side view of the user interface device as shown in FIG. 1 under deformation due to air pressure.

Referring to FIG. 5, a schematic a schematic side view of the user interface device 10 under deformation due to air pressure is illustrated in accordance with embodiments of the present invention. The user interface device 10 includes a cushion 20 adapted for contacting the user's face, a base 14, a customized element 15, and means for joining the customized element 15 with the cushion 20. Cushion 20 is a flexible structure provided to a substantially rigid frame member, the base 14, and adapted to engage with the user's face. Cushion 20 includes a facial interface 11 adapted for contacting the user's face and a support interface 13 positioned between the facial interface 11 and the base 14. The facial interface 11 includes a core 18 adapted for providing flexibility and strength. The facial interface 11 further includes an integrated air tight-flap 17 adapted to engage with the user's face. The support interface 13 includes a core 19 adapted for providing flexibility and strength. A pressure distribution line 28 representing the pressure distribution at the facial interface 11 is shown for deformation of the user interface device 10 under gas pressure.

Referring to FIGS. 2 to 4, it is illustrated that the customized element 15 keeps the facial interface 11 and, thus, the user interface device 10, compliant with the user's face independently of the mask deformations caused, for example, by the horizontal forces 22 (FIG. 2), the vertical forces 24 (FIG. 3), due to the device 10 being pulled aside (line 26, FIG. 4) and due to gas pressure (line 28, FIG. 5). By designing customized element 15 according to the above mentioned specifications, customized element 15 is adapted to keep the facial interface 11 compliant with the user's face independently of the deformations of the user interface device 10, which gives extra freedom in the design of support interface 13. Moreover, by changing the orthogonal cross-section of customized element 15, the rigidity of cushion 20 to horizontal deformations (in the facial plane) and to vertical deformations (orthogonal to the facial plane) may be independently controlled, as illustrated in FIGS. 2 and 3. For example, the cross-section of customized element 15 may be elongated in the facial plane, as it is shown in FIG. 1. In this case, customized element 15 may effectively resist horizontal deformations 22 (FIG. 2) while giving more freedom in vertical deformations 24 (FIG. 3). The support interface 13 may be effectively freed from being responsible for the shape of the facial interface 11 and, therefore, may be allow additional freedom in the position of the user interface device 10, as shown in FIG. 4 and the range of air pressures, as shown in FIG. 5.

In an embodiment of the present invention, the customized element 15 and the cushion 20 as described above will be supplied in a kit of parts for manufacturing the user interface device 10 for delivering gas to a user's face. The kit of parts may further include means for joining the customized element 15 with the cushion 20. Such means may be provisions for embedding the customized element 15 within the user interface device, for example hollow spaces such as chamber 20, or provisions for surface mounting the customized element 15, such as mechanical connectors.

A method for customizing the user interface device 10 for delivering a gas to a user, for example, during CPAP therapy, the device having an surface interface 11 adapted for fitting to at least one user specific body feature, in accordance with embodiments of the present invention may include the steps of providing a user specific data set representing an e.g. three-dimensional shape of the at least one user specific body feature and manufacturing a customized element 15 according to the user specific data set such that the customized element 15 is adapted to affect the shape of the surface interface 11. In a further step may the user interface device 10 may be connected to at least one part of the user interface device and thereby deforming the at least one part of the user interface device according to the user specific data set. In a still further step may the customized element 15 be manufactured utilizing a rapid prototyping technology or modifying the shape of a mass-produced blank element. Further included may be the preliminary step of pre-fabricating a cushion 20 of the user interface device to include a chamber 12 open to the outer surface of cushion 12 (FIG. 1). In a further preliminary step, the face of a user, which may be, for example, a patient, may be scanned to obtain data from which a 3D image is derived or a cast may be made of the face and the cast is scanned from which the 3D image is produced. In a still further step, a customized element 15 may be manufactured according to the obtained 3D data. The customized element 15 is then in a further step inserted into chamber 12 through opening 16, thereby deforming cushion 20 according to the facial features of the user. In a further step, customized element 15 may keep surface interface 11 compliant with the face of the user under a wide range of deformations of the user interface device 10, thereby providing extra freedom to the position of the user interface device 10 and the range of applied air pressures. As a result, the user interface device 10 may be comfortably worn by the user for extended periods of time. In a still further step, customized element 15 may be removed from chamber 12 and may be reused in a different cushion. Accordingly, embodiments of the present invention enable cost effective customization of otherwise standard user interface devices resulting in increased comfort for users.

In a further embodiment of the present invention, a method of manufacturing the customized element 15 for adapting to the user interface device 10 for delivering gas to a user, for example, during CPAP therapy, comprises the steps of obtaining a user specific data set representing at least partially the tree-dimensional shape of the user's face and pre-forming a rigid or semi-rigid structure according to the obtained data. In a further step, supplementary user specific data related to the sensitivity and thickness of the skin of the user's face are obtained and the rigid structure is pre-formed in accordance with the supplementary data. The pre-forming of the structure and, thus, the customized element 15, is done in a further step by utilizing a rapid prototyping technology or, alternatively, by modifying the shape of a mass-produced blank element.

In accordance with further embodiments of the present invention, the customized element 15 comprises a rigid or semi-rigid structure that has a shape that is different from the ring shown in FIG. 2. The customized element 15 may be made of a plurality of parts instead of the single part shown in FIG. 2. For example, the customized element may includes two separate parts, where a first part is formed according a first facial area, such as the nasal area, for example, and where a second part is formed according to a second facial area, such as the chin area, for example. Both parts may then be aligned relative to each other to form a loop and with relatively small spaces between each other. Such arrangement may have the advantage of providing a cushion 20 having more flexibility in the areas of the spaces between the adjacent parts of the customized element 15. The customized element 15 can be mechanically connected to the cushion 20 using a variety of fasteners known in the art. The customized element 15 can further be positioned outside of the cushion 20. For example, cushion 20 can be placed between base 14 and support interface 13.

In accordance with a further embodiment of the present invention, the cushion 20 can be a customized part with an integral customized element 15. For example, the customized element 15 can be molded into the cushion 20.

In accordance with still a further embodiment of the present invention, the shape of the customized element 15 is adapted to be changeable after being first pre-formed to correspond to the shape of a user's face. This is achieved by selecting a material for the customized element that is relatively rigid at room temperature, but formable at higher temperatures. For example, customized element 15 is adapted for re-adjusting after initial forming and after insertion into chamber 12 of cushion 10 by heating. The heating is done such that the temperature of the customized element 15 is increased while the cushion 20 stays at ambient temperature. Such is achieved with a spiral resistor wire integrated into customized element 15. Alternatively, the customized element 15 can be produced using materials which absorb microwaves (and, thus, can be heated in microwave oven) or by using materials which can be heated in induction oven; e.g. materials containing some metal particles or atoms in the material of customized element 15. Thus, it is then possible to heat cushion 20 along with the integrated customized element 15 in a microwave oven, or by induction, to heat customized element 15 while cushion 20 remains cold. Customized element 15 can further be formed such that it is pliable only in certain areas, such as the nasal or nasal-mouth area or the forehead support area. If pliability is desirable only in certain areas, pliable elements may be included only in such areas.

In accordance with still a further embodiment of the present invention, the customized element 15 can be pre-formed in accordance to an average shape of a human face where the average is, for example, taken over a certain population of people (e.g. OSA patients, Asian faces, Afro-American faces, etc.). The average can further be taken according to gender or age or other characteristics that are common for a relatively large number of people.

Figure 6:
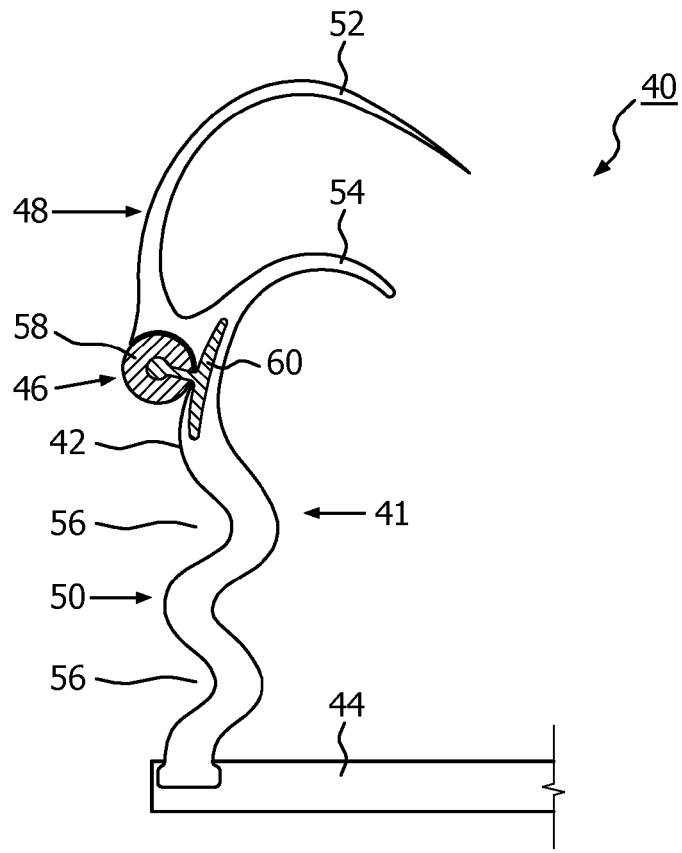
FIG. 6 is a schematic cross-sectional view of a user interface device according to an alternative embodiment of the invention.

FIG. 6 is a schematic cross-sectional view of a user interface device 40 according to an alternative embodiment of the invention. User interface device 40 includes a customizable cushion assembly 41 that is coupled to a base 44, which in the exemplary embodiment is a substantially rigid or semi-rigid frame member. The cushion assembly 41 includes a cushion 42 adapted for contacting the user's face, and a customized element assembly 46, described in greater detail below, coupled to cushion 42. Customized element assembly 46 affects at least partially the shape of cushion 42. Cushion 42 is a flexible structure coupled to the substantially rigid or semi-rigid base 44, and is adapted to engage with the user's face. In the exemplary embodiment, cushion 42 is made of a soft, flexible, cushiony, elastomeric material, such as, without limitation, silicone, an appropriately soft thermoplastic elastomer, a closed cell foam, or any combination of such materials, and base 44 is formed from a substantially rigid or semi-rigid material, such as, without limitation, a polycarbonate or an injection molded thermoplastic. Cushion 42 may engage with certain areas of a user's face, such as, without limitation, the chin area, the mouth area, the nasal area, the nasal-mouth area, the forehead area or may outline of the entire user interface device.

Cushion 42 includes a facial interface portion 48 adapted for contacting the user's face and a support interface portion 50 positioned between facial interface portion 48 and base 44. Facial interface portion 48 is typically optimized for maximum comfort for the users and support interface portion 50 is typically optimized for flexibility and support of cushion 42. As seen in FIG. 6, facial interface portion 48 includes an integrated sealing flap 52 adapted to engage with the user's face, and an integrated supporting flap 54 positioned beneath sealing flap 52. In alternative embodiments, sealing flap 52 and supporting flap 54 can be separate parts. In the exemplary embodiment, due to the usage and functionality of customized element assembly 46, facial interface portion 48 does not need to have a role in controlling the shape of cushion 42 and, therefore, can be made from a flexible material to be extra soft. The support interface portion 50 includes grooves 56 adapted for providing flexibility and strength. In addition, support interface portion 50 can contain spring like elements embedded in such material. As seen in FIG. 6, support interface portion 50 is mechanically connected with base 44 by any suitable means.

Customized element assembly 46 is, in the present embodiment, a two piece assembly that includes a customized element 58 that is removeably coupled to and held by a holder element 60. As described in greater detail herein, customized element assembly 46 is structured to enable user interface device 40 to be customized to fit the face of a particular user.

Figure 7:
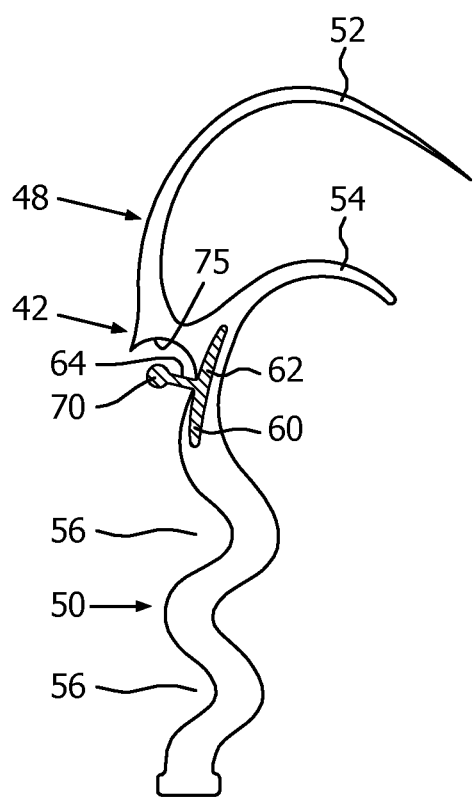
FIG. 7 is a schematic cross-sectional view of a customizable cushion assembly forming a part of the user interface device of FIG. 6.

Holder element 60 is coupled to and extends from the upper part of support interface portion 50 of cushion 42, and is structured to extend at least partially along a contour of user interface device 40. In one particular, non-limiting embodiment, holder element 60 has an annular shape and extends around the entire upper periphery of support interface portion 50. As used herein, "annular" shall refer to both a circular and a non-circular surrounding boundary, such as a circular or non-circular ring. In the exemplary embodiment, holder element 60 is a mold insert that is used during the molding of cushion 42 such that cushion 42 is over-molded on top of holder element 60, making holder element 60 integrally attached to support interface portion 50 as shown in FIG. 7. Also in the exemplary embodiment, holder element 60 is made of a material that is harder than the material of cushion 42, such as, without limitation, a polycarbonate or thermoplastic material, yet still allows for free bending of holder element 60 in all directions. For example, cushion 42 may be made of a material, such as silicone, a thermoplastic elastomer, or a closed cell foam, and holder element 60 may be made of a material, such as polycarbonate, a thermoplastic, polyoxymethylene (POM) (commonly known as acetal), polyamide (PA) (commonly known as nylon, including PA66 and PA12), or a high heat resisting polymer such as polyetherimide (PEI) (commercially known as Ultem®), wherein the durometer of holder element 60 is greater than the durometer of cushion 42. In addition, to facilitate such free bending, holder element 60 may be made with interleaved thicker and thinner sections along the length thereof.

Figure 8:
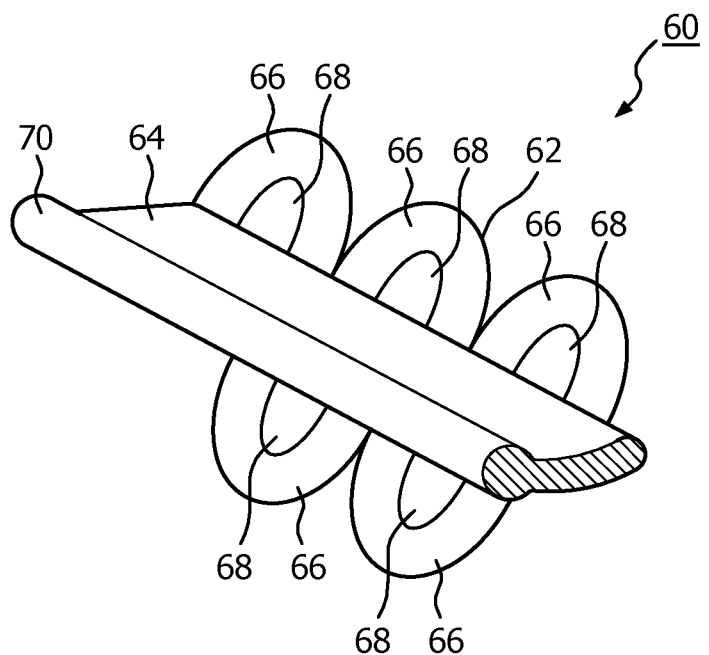
FIG. 8 is an isometric view of a portion of a holder element of the customizable cushion assembly forming a part of the user interface device of FIG. 6.

FIG. 8 is an isometric view of a portion of holder element 60 according to the exemplary embodiment. As seen in FIG. 8, as well as in FIGS. 6 and 7, holder element 60 includes a base portion 62 and an extension member 64 extending from base portion 62. In the exemplary embodiment, extension member 64 extends in a direction that is substantially perpendicular to the top planar surface of base portion 62. Also in the exemplary embodiment, as seen in FIG. 8, base portion 62 has a shape that facilitates the anchoring and integration of holder element 60 into support interface portion 50 during the molding process. In the illustrated, non-limiting embodiment, base portion 62 includes a plurality of arc-shaped portions 66 defining orifices 68 for this purpose. In addition, extension member 64 includes an enlarged portion 70 at the distal end thereof. In the illustrated embodiment, enlarged portion 70 is rounded, although other shapes are also possible.

Figure 9:
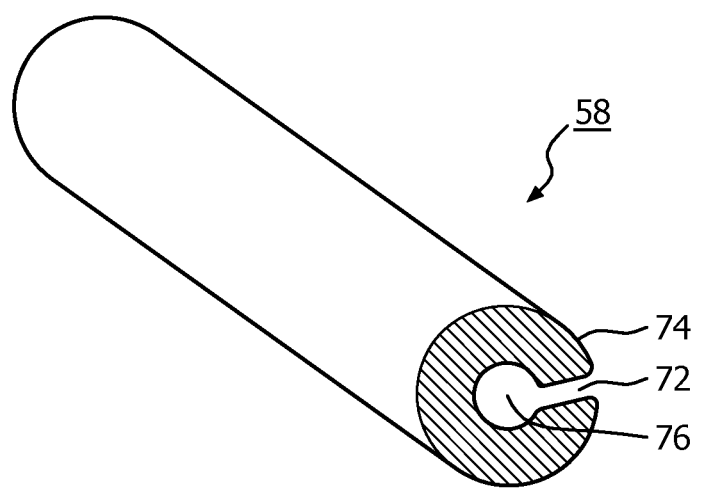
FIG. 9 is an isometric view of a portion of a customized element of the customizable cushion assembly forming a part of the user interface device of FIG. 6.

FIG. 9 is an isometric view of a portion of customized element 58 according to the exemplary embodiment. Customized element 58 has a generally round cross-sectional shape and includes a gap 72 provided in a first side 74 thereof that leads to an internal slot or groove 76 that is complimentary to the shape of enlarged portion 70. Customized element 58 is structured to be selectively attached to holder element 60 when holder element 60 is integrally coupled to cushion 42 as described above. In particular, customized element 58 is structured to be "snapped" or "clicked" onto holder element 60 by way of enlarged portion 70 of holder element 60 being removeably received within slot or groove 76 of customized element 58 through gap 72 as shown in FIG. 6 (as will be appreciated, first side 74 will temporarily flex/expand to allow enlarged portion 70 to pass through gap 72 to slot or groove 76). When this is done, customized element 58 will be received within an arc-shaped channel 75 provided in cushion 42 beneath the first end of each of sealing flap 52 and supporting flap 54 such that sealing flap 52 and supporting flap 54 rest on customized element 58.

Furthermore, customized element 58, like customized element 15 described elsewhere herein in connection with the embodiment of FIGS. 1-5, comprises a pre-formed rigid or semi-rigid structure adapted for corresponding to the shape of the user's face and adapted for extending at least partially along a contour of user interface device 40. In one particular, non-limiting embodiment, customized element 58 extends around the entire periphery of the user interface device 40. In the exemplary embodiment, the particular shape of customized element 58 is based on a user specific data set representing the three-dimensional shape of a portion of the user's face. In one embodiment, the shape of customized element 58 is not changeable after being first pre-formed according to the shape of the user's face.

In the exemplary embodiment, customized element 58 is fabricated independently and separately from user interface device 40 and, when coupled to holder element 60 to form customized element assembly 46 as described herein, affects the shape of sealing interface portion 48 and is responsible for the optimal pressure distribution at sealing interface portion 48 of user interface device 40. Customized element 58 is, when coupled to holder element 60, adapted to pre-deform cushion 42, and specifically sealing interface portion 48, making it compliant with a given face of a particular user. Customized element 58, like customized element 15, is a custom fabricated element, where the shape is adapted to match a user specific data set representing the shape of the user's face. As described in detail elsewhere herein, the data set may be, for example, obtained from a three-dimensional (3D) scan of the user's face (or using other methods as described herein), and can include data from the entire face of the user or only from certain parts, such as the nose, chin, forehead, or cheeks. Moreover, customized element 58 may be fabricated from the same or similar materials as customized element 15 using the same or similar fabrication techniques, each of which is described in greater detail herein in connection with customized element 15.

Thus, customized element assembly 46 comprising customized element 58 coupled to and held by holder element 60 is structured to keep the sealing interface portion 48 and, therefore, user interface device 40, compliant with the user's face independently of the mask deformations that may be caused by, for example, horizontal forces on user interface device 40, vertical forces on user interface device 40, and/or gas pressure.

In one alternative embodiment, rather than employing a single holder element 60 having an annular shape that extends around the entire periphery of support interface portion 50, user interface device 40 may employ a plurality of individual holder elements 60 that are spaced around the periphery of support interface portion 50 for receiving and holding customized element 58 as described herein.

In another alternative embodiment, rather than employing a single customized element 58 that extends around the entire periphery of support interface portion 50, user interface device 40 may employ a plurality of smaller individual customized elements 58 that are spaced around the periphery of support interface portion 50. In this embodiment, each such smaller individual customized element 58 may be coupled to a single holder element 60 that extends around the entire periphery of support interface portion 50, or to one or more individual holder elements 60 that are spaced around the periphery of support interface portion 50 as described above.

Figure 10:
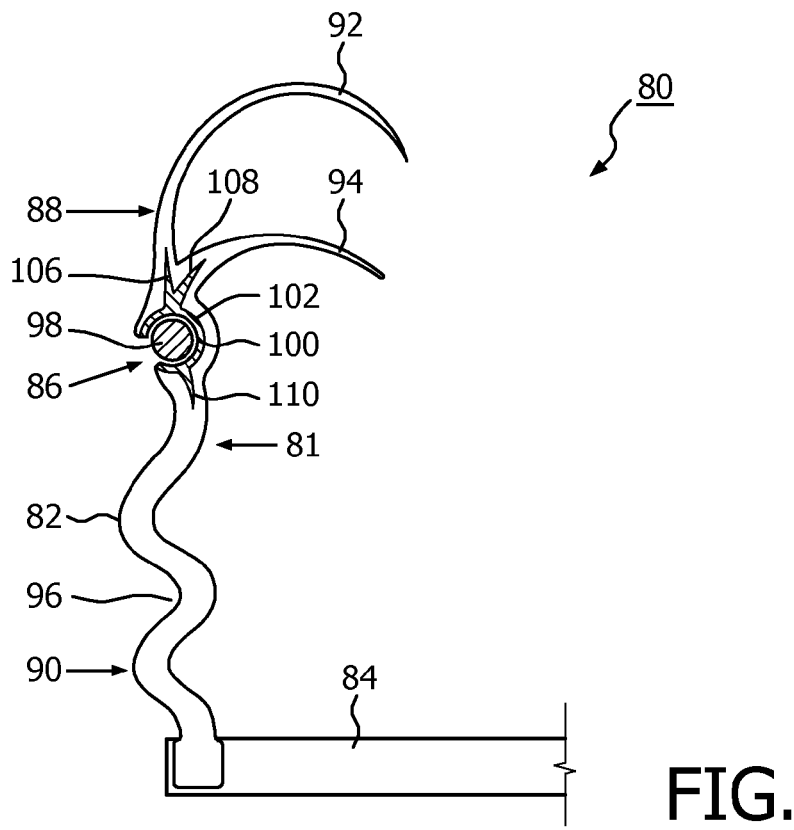
FIG. 10 is a schematic cross-sectional view of a user interface device according to another alternative embodiment of the invention.

FIG. 10 is a schematic cross-sectional view of a user interface device 80 according to another alternative embodiment of the invention. User interface device 80 is similar to user interface device 40 and includes a customizable cushion assembly 81 that is coupled to a base 84, which in the exemplary embodiment is a substantially rigid or semi-rigid frame member. Cushion assembly 81 includes a cushion 82 adapted for contacting the user's face, and a customized element assembly 86, described in greater detail below, coupled to cushion 82. Customized element assembly 86 affects at least partially the shape of cushion 82. Cushion 82 is a flexible structure coupled to the substantially rigid or semi-rigid base 84, and is adapted to engage with the user's face. In the exemplary embodiment, cushion 82 is similar to cushion 42 and is made of a soft, flexible, cushiony, elastomeric material, such as, without limitation, silicone, an appropriately soft thermoplastic elastomer, a closed cell foam, or any combination of such materials, and base 84 is similar to base 44 and is formed from a rigid or semi-rigid material, such as, without limitation, a polycarbonate or an injection molded thermoplastic. Cushion 82 may engage with certain areas of a user's face such as the chin area, the mouth area, the nasal area, the nasal-mouth area, the forehead area or may outline of the entire user interface device.

Cushion 82 includes a facial interface portion 88 adapted for contacting the user's face and a support interface portion 90 positioned between facial interface portion 88 and base 84. Facial interface portion 88 is typically optimized for maximum comfort for the users and support interface portion 90 is typically optimized for flexibility and support of cushion 82. Facial interface portion 88 includes an integrated sealing flap 92 adapted to engage with the user's face, and an integrated supporting flap 94 positioned beneath sealing flap 92. In the exemplary embodiment, due to the usage of customized element assembly 86, facial interface portion 88 does not need to have role in controlling the shape of cushion 82 and, therefore, can be made from a flexible material to be extra soft. The support interface portion 90 includes one or more grooves 96 adapted for providing flexibility and strength. In addition, support interface portion 90 can contain spring like elements embedded in such material. As seen in FIG. 10, support interface portion 90 is mechanically connected with base 84.

Customized element assembly 86 is, like customized element assembly 46, a two piece assembly that includes a customized element 98 removeably coupled to and held by a holder element 100. As described in greater detail herein, customized element assembly 86 is structured to enable user interface device 80 to be customized to fit the face of a particular user.

Figure 11:
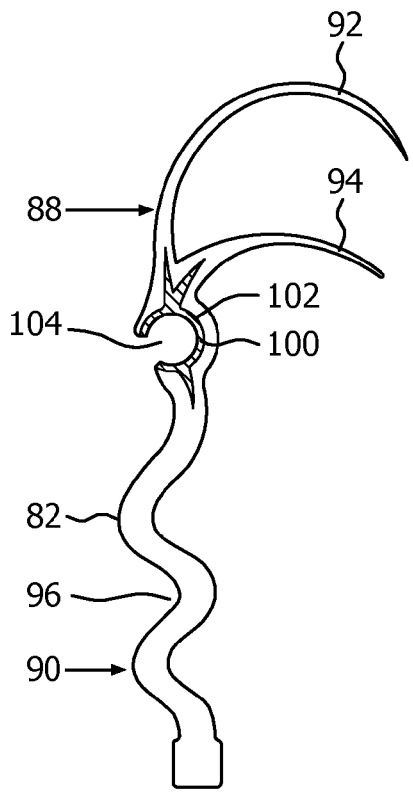
FIG. 11 is a schematic cross-sectional view of a customizable cushion assembly forming a part of the user interface device of FIG. 10.

Holder element 100 is coupled to cushion 82, and is structured to extend at least partially along a contour of user interface device 80. In one particular, non-limiting embodiment, holder element 100 has an annular shape and extends around the entire periphery of cushion 82. In the exemplary embodiment, holder element 100, like holder element 60, is a mold insert that is used during the molding of cushion 82 such that cushion 82 is overmolded on top of holder element 100, making holder element 100 integrally attached to cushion 82 as shown in FIG. 11. Also in the exemplary embodiment, holder element 100 is made of a material that is harder than the material of cushion 82, such as, without limitation, a polycarbonate or thermoplastic material, yet still allows for free bending of holder element 100 in all directions. For example, cushion 82 may be made of a material, such as silicone, an elastomer or a closed cell foam, and holder element 100 may be made of a material, such as polycarbonate, thermoplastic, polyoxymethylene (POM) (commonly known as acetal), polyamide (PA) (commonly known as nylon, including PA66 and PA12), or a high heat resisting polymer such as polyetherimide (PEI) (commercially known as Ultem®), wherein the durometer of holder element 100 is greater than the durometer of cushion 82. To facilitate such free bending, holder element 100 may be made with interleaved thicker and thinner sections along the length thereof.

Figure 12:
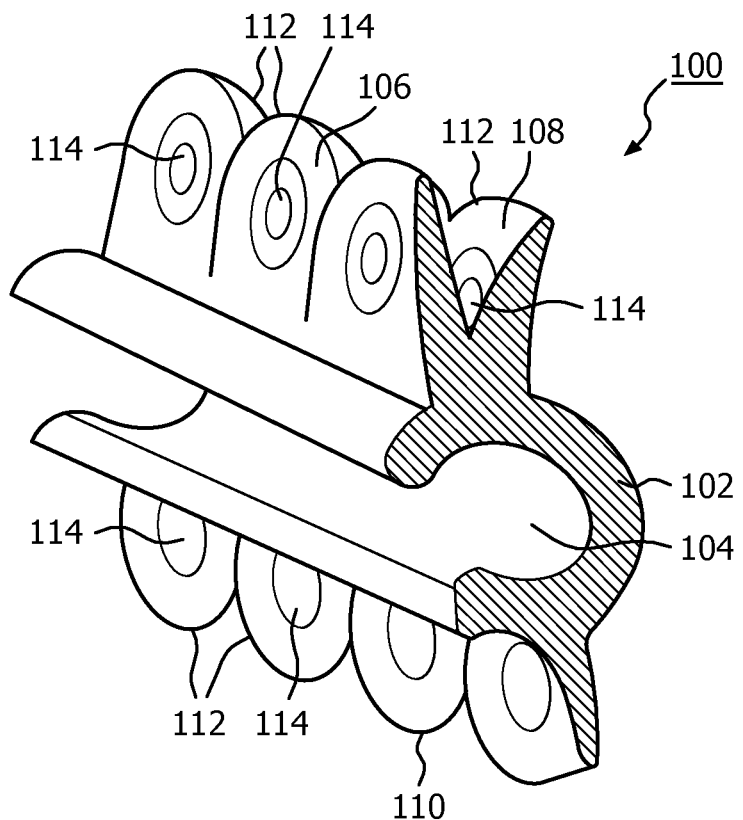
FIG. 12 is an isometric view of a portion of a holder element of the customizable cushion assembly forming a part of the user interface device of FIG. 10.
Figure 13:
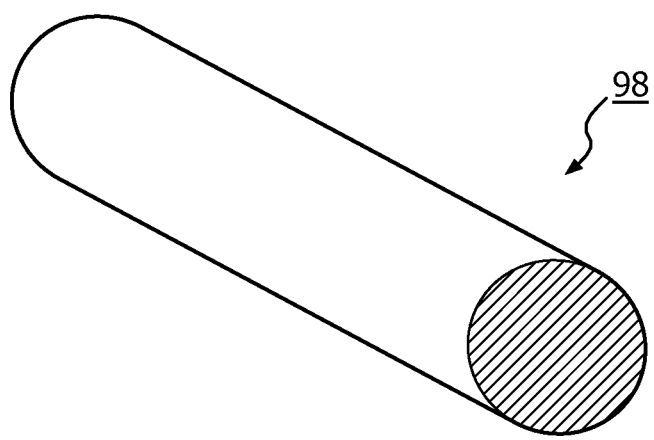
FIG. 13 is an isometric view of a portion of a customized element of the customizable cushion assembly forming a part of the user interface device of FIG. 10.

FIG. 12 is an isometric view of a portion of holder element 100 according to the exemplary embodiment. As seen in FIG. 12, as well as in FIGS. 10 and 11, holder element 100 includes an arc-shaped central portion 102 defining a round channel 104. Holder element 100 also includes first and second anchor portions 106, 108, respectively, extending from a top side of central portion 102, and a third anchor portion 110 extending from a bottom side of central portion 102. As seen in FIGS. 10 and 11, first anchor portion 106 extends partially within sealing flap 92, second anchor portion 108 extends partially within supporting flap 94, and third anchor portion 110 extends partially within support interface portion 90. In the exemplary embodiment, as seen in FIG. 13, anchor portions 106, 108 and 110 each has a shape that facilitates the anchoring and integration of holder element 100 into facial interface portion 88 and support interface portion 90 during the molding process. In the illustrated, non-limiting embodiment, anchor portions 106, 108 and 110 each includes a plurality of arc-shaped portions 112 defining orifices 114 for this purpose.

FIG. 13 is an isometric view of a portion of customized element 98 according to the exemplary embodiment. Customized element 98 has a generally round cross-sectional shape that is complimentary to the shape of channel 104. Customized element 98 is structured to be selectively attached to holder element 100 when holder element 100 is integrally coupled to cushion 82 as described above. In particular, customized element 98 is structured to be "snapped" or "clicked" into holder element 100 by being removeably inserted into channel 104 as shown in FIG. 10 (as will be appreciated, central portion 102 of holder element 100 will temporarily flex/expand to allow customized element 98 to be received in channel 104).

Furthermore, customized element 98, like customized elements 58 and 15 described elsewhere herein, comprises a pre-formed rigid or semi-rigid structure adapted for corresponding to the shape of a portion of the user's face and adapted for extending at least partially along a contour of the user interface device 80. In one particular, non-limiting embodiment, customized element 98 extends around the entire periphery of the user interface device 80. In the exemplary embodiment, the particular shape of customized element 98 is based on a user specific data set representing the three-dimensional shape of the user's face, and in one embodiment, the shape of customized element 98 is not changeable after being first pre-formed according to the shape of the user's face.

In the exemplary embodiment, customized element 98, like customized elements 58 and 15 described elsewhere herein, is fabricated independently and separately from the user interface device 80 and, when coupled to holder element 100 to form customized element assembly 86 as described herein, affects the shape of sealing interface portion 88 and is responsible for the optimal pressure distribution at sealing interface portion 88 of user interface device 80. Customized element 98 is, when coupled to holder element 100, adapted to pre-deform cushion 82, and specifically the sealing interface portion 88, making it compliant with a given face of a particular user. Customized element 98, like customized elements 58 and 15, is a custom fabricated element, where the shape is adapted to match a user specific data set representing the shape of the user's face obtained as described in detail elsewhere herein. Moreover, customized element 98 may be fabricated from the same or similar materials as customized elements 15 and 58, using the same or similar fabrication techniques.

Thus, customized element assembly 86 comprising customized element 98 coupled to and held by holder element 100 is structured to keep the sealing interface portion 88 and, therefore, user interface device 80, compliant with the user's face independently of the mask deformations that may be caused by, for example, horizontal forces on user interface device 80, vertical forces on user interface device 80, and/or gas pressure.

In one alternative embodiment, rather than employing a single holder element 100 having an annular shape that extends around the entire periphery of cushion 82, user interface device 80 may employ a plurality of individual holder elements 100 that are spaced around the periphery of cushion 82 for receiving and holding customized element 98 as described herein.

In another alternative embodiment, rather than employing a single customized element 98 that extends around the entire periphery of cushion 82, user interface device 80 may employ a plurality of smaller individual customized elements 98 that are spaced around the periphery of cushion 82. In this embodiment, each such smaller individual customized element 98 may be coupled to a single holder element 100 that extends around the entire periphery of cushion 82, or to one or more individual holder elements 100 that are spaced around the periphery of cushion 82 as described above.

Figure 14:
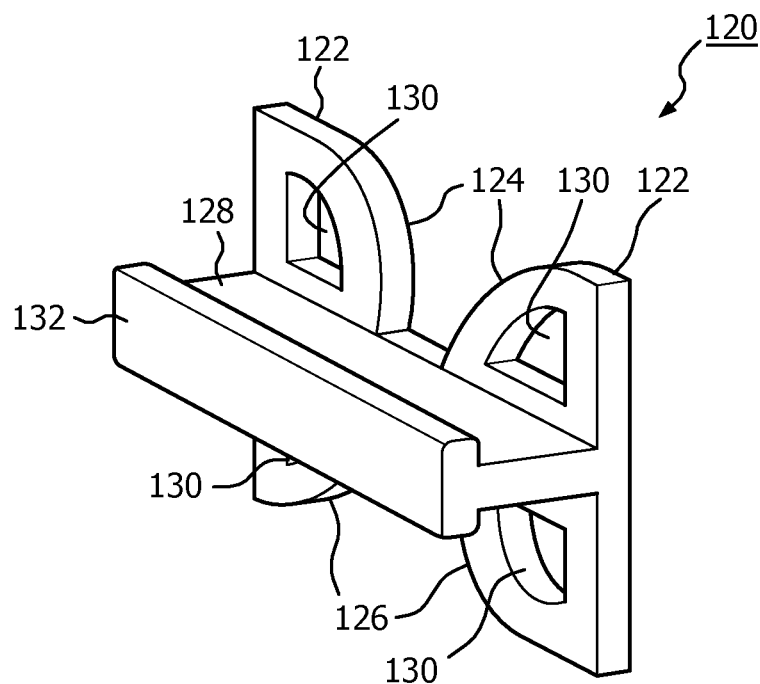
FIG. 14 is an isometric view and FIG. 15 is a top plan view of a portion of a holder element according to an alternative exemplary embodiment of the invention.
Figure 15:
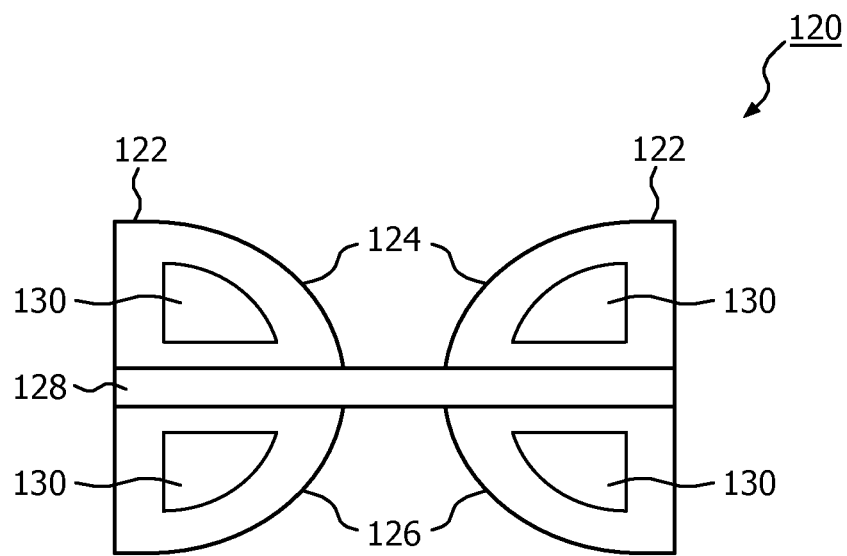

FIG. 14 is an isometric view and FIG. 15 is a top plan view of a portion of a holder element 120 according to an alternative exemplary embodiment of the invention. Holder element 120 may be used in place of holder element 60 for coupling to customized element 58 as described elsewhere herein. As seen in FIGS. 14 and 15, holder element 120 has a chain structure. More specifically, holder element 120 includes a plurality of base portions 122 each including an upper portion 124 and a lower portion 126, wherein the base portions 122 are spaced along the length of holder element 120 (like the links of a chain). Holder element 120 also includes an extension member 128 extending from the front side of base portions 122, which serve to connect base portion 122 together. In the exemplary embodiment, extension member 128 extends in a direction that is substantially perpendicular to the top planar surface of base portions 122. Also in the exemplary embodiment, as seen in FIGS. 14 and 15, each base portion 122 has a shape that facilitates the anchoring and integration of holder element 120 into support interface portion 50 during the molding process. In the illustrated, non-limiting embodiment, each upper portion 124 and lower portion 126 has a pie shape defining an orifice 130 for this purpose. In addition, extension member 128 includes an enlarged portion 132 at the distal end thereof. In the illustrated embodiment, enlarged portion 132 is rounded, although other shapes are also possible.

The embodiment of FIGS. 14 and 15 thus provides a structure that allows free 3-dimensional deformation of holder element 120, while at the same time enabling every base portion 122 to securely couple to customized element 58. Thus, holder element 120 is rigid enough to hold customized element 58 in order to follow exactly its custom geometry, yet is soft enough such that it does not influence the geometry of customized element 58. For this purpose, holder element 120 may be made of a material, such as polycarbonate, thermoplastic, polyoxymethylene (POM) (commonly known as acetal), polyamide (PA) (commonly known as nylon, including PA66 and PA12), or a high heat resisting polymer such as polyetherimide (PEI) (commercially known as Ultem®).

Figure 16:
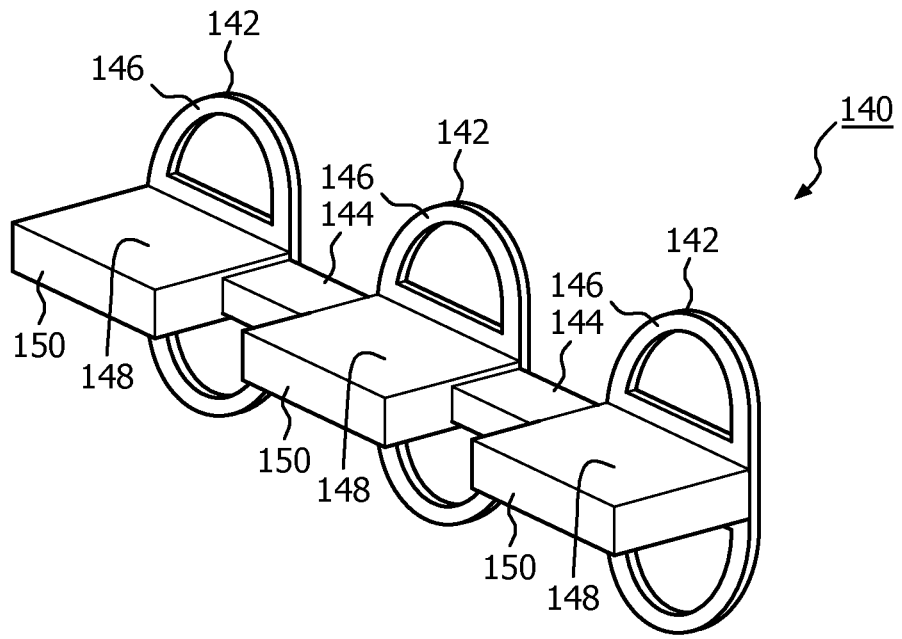
FIG. 16 is an isometric view and FIG. 17 is a top plan view of a portion of a holder element according to another alternative exemplary embodiment of the invention.
Figure 17:
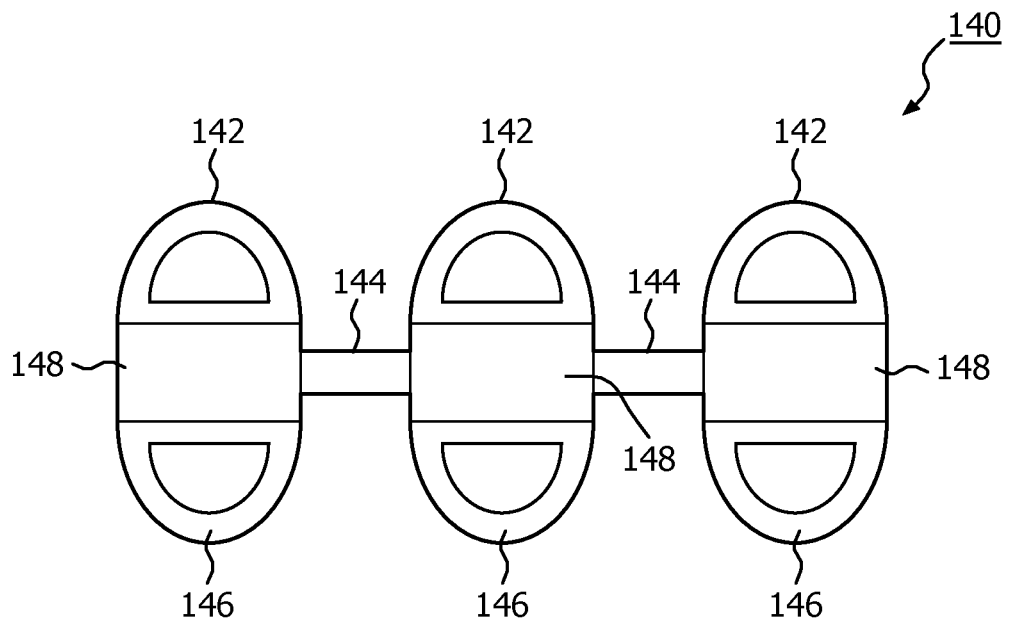

FIG. 16 is an isometric view and FIG. 17 is a top plan view of a portion of a holder element 140 according to another alternative exemplary embodiment of the invention. Holder element 140, like holder element 120, may be used in place of holder element 60 for coupling to customized element 58 as described elsewhere herein. As seen in FIGS. 16 and 17, holder element 140 also has a chain structure. More specifically, holder element 140 includes a plurality of holder portions 142 that are spaced along the length of holder element 140 (like the links of a chain), wherein immediately adjacent pairs of holder portions 142 are held to one another by a linking portion 144 (molded from the same material as holder portions 142, e.g., polycarbonate or thermoplastic). Each holder portion 142 includes a base portion 146 having upper and lower arc-shaped members each defining an orifice, and an extension member 148 extending from the front side of the holder portion 142. In the exemplary embodiment, each extension member 148 extends in a direction that is substantially perpendicular to the top planar surface of the associated holder portion 142.

Also in the exemplary embodiment, as seen in FIGS. 14 and 15, each base portion 146 has a shape that facilitates the anchoring and integration of holder element 140 into support interface portion 50 during the molding process (i.e., the orifices described above). In addition, each extension member 148 includes an enlarged portion 150 at the distal end thereof. In the illustrated embodiment, each enlarged portion 150 is rounded, although other shapes are also possible.

The embodiment of FIGS. 16 and 17, like the embodiment of FIGS. 14 and 15, thus provides a structure that allows free 3-dimensional deformation of holder element 140, while at the same time enabling every holder portion 142 to securely couple to customized element 58. Thus, holder element 140 is rigid enough to hold customized element 58 in order to follow exactly its custom geometry, yet is soft enough such that it does not influence the geometry of customized element 58. For this purpose, holder element 140 may be made of a material, such as polycarbonate, thermoplastic, polyoxymethylene (POM) (commonly known as acetal), polyamide (PA) (commonly known as nylon, including PA66 and PA12), or a high heat resisting polymer such as polyetherimide (PEI) (commercially known as Ultem®).

Other arrangements for accomplishing the objectives of embodiments of the present invention will be obvious for those skilled in the art.

In accordance with the above described embodiments, the present invention enables cost effective customization of otherwise standard user interface devices resulting in increased comfort for users.

It is to be understood that although preferred embodiments, specific constructions and configurations, as well as materials, have been discussed herein for devices according to the present invention, various changes or modifications in form and detail may be made without departing from the scope and spirit of this invention. For example, the user interface device may be a flexible shell mask that can be adapted for fitting to at least one user specific body feature with the customized element according to embodiments of the present invention. In this case, a user interface device assembled together with accompanying customized element may, for example, look like a flexible mask shell with the customized element running along, e.g. the (internal and/or external) periphery or one or more parts of the (internal and/or external) periphery of the user interface device. To the latter end, the customized element may comprise a plurality of (not necessarily connected) parts.

The invention claimed is:

1. A customizable mask element for a user interface device, said user interface device comprising a surface interface adapted for contacting a user's face, wherein the customizable mask element is either a cushion or a mask shell and comprises:
   means for receiving and connecting a non-integrated customized element in a manner wherein the customized element affects a shape of the surface interface of the user interface device according to at least one body feature specific to the user,
   wherein said means for receiving and connecting the customized element is arranged outside of a breathing path of the mask element wherein said means for receiving and connecting the customized element includes a holder element, the holder element being structured to removably receive and hold the customized element in a manner wherein the customized element when held by the holder element affects the shape of the surface interface according to the at least one body feature specific to the user, and where the holder element is made of a material having a durometer that is greater than a durometer of a material of the cushion, and wherein the holder is integrally formed as part of the cushion during molding of the cushion.

2. The customizable mask element according to claim 1, wherein said means for receiving and connecting the customized element includes a chamber for receiving the customized element in a manner wherein the customized element when received within the chamber affects the shape of the surface interface according to the at least one body feature specific to the user.

3. The customizable mask element user interface device according to claim 1, further comprising the customized element, wherein a shape of the customized element is determined based on a user specific data set representing a shape of the at least one body feature specific to the user.

4. A user interface device, comprising the customizable mask element as claimed in claim 1.

5. A customizable mask element for a user interface device, said user interface device comprising a surface interface adapted for contacting a user's face, wherein the customizable mask element is either a cushion or a mask shell and comprises:
   means for receiving and connecting a non-integrated customized element in a manner wherein the customized element affects a shape of the surface interface of the user interface device according to at least one body feature specific to the user,
   wherein said means for receiving and connecting the customized element is arranged outside of a breathing path of the mask element, wherein said means for receiving and connecting the customized element includes a holder element, the holder element being structured to removably receive and hold the customized element in a manner wherein the customized element when held by the holder element affects the shape of the surface interface according to the at least one body feature specific to the user, and wherein the holder element comprises a chain structure comprising a plurality of base portions spaced along a length of the holder element, wherein each immediately adjacent pair of the base portions is linked to one another.

6. A customized element assembly adapted for connection with a customizable cushion for delivering a gas to a user, the customizable cushion having a surface interface adapted for contacting a user's face, the customized element assembly comprising:
   a customized element having a first shape determined based on a user specific data set representing a shape of at least one body feature specific to the user, the customized element being structured to positioned in the cushion outside of the breathing path of the cushion in a manner wherein the customized element affects a second shape of the surface interface according to the first shape of the customized element, and
   a holder element, the customized element being structured to be removably received and held by the holder element in a manner wherein the customized element affects the second shape of the surface interface according to the first shape of the customized element, and wherein, (i) the customized element includes an internal groove structured to receive and hold an enlarged portion of the holder element, or (ii) the holder element comprises a portion defining a channel, and the customized element has a cross-sectional shape that is complimentary to a shape of the channel to enable the portion to receive and hold the customized element, and wherein the holder element and the customized element are made of a material having a durometer that is greater than a durometer of a material of the cushion.

7. The customized element according to claim 6, wherein the customized element is manufactured to have the first shape based on a user specific data set representing a shape of the at least one body feature specific to the user.

8. The customized element assembly according to claim 6, wherein the customized element consists of several parts and/or wherein the customized element is fabricated from a metallic spring material or plastic.

9. The customized element assembly according to claim 6, wherein the shape of the customized element is: (i) not changeable after being first adapted to have the first shape, or (ii) changeable after being first adapted to have the first shape.

10. A user interface device including the customized element assembly according to claim 6.

11. A method of customizing a customizable user interface device for delivering a gas to a user, the customizable user interface device having a surface interface adapted for contacting a user's face, the method comprising the steps of:

providing a user specific data set representing a shape of at least one body feature specific to the user;

manufacturing a customized element to have a first shape determined according to the user specific data set such that the customized element is adapted to affect a second shape of the surface interface when the customized element is coupled to the user interface device, connecting the manufactured customized element to the user interface device, such that the customized element is arranged outside of a breathing path.

12. Method of providing a customized element adapted for connection with a customizable user interface device outside of a breathing path, including the steps of:

receiving or determining a user specific data set representing a shape of at least one body feature specific to the user, and using the user specific data set for determining a structure of the customized element having a first shape, manufacturing the customized element or selecting a customized element suitable for the user from a predetermined set of patient interfaces.

* * * * *